US012593990B2

(12) United States Patent
Zhi et al.

(10) Patent No.: US 12,593,990 B2
(45) Date of Patent: Apr. 7, 2026

(54) SYSTEM AND METHODS UTILIZING ARTIFICIAL INTELLIGENCE ALGORITHMS TO ANALYZE WEARABLE ACTIVITY TRACKER DATA

(71) Applicant: Aetna Inc., Hartford, CT (US)

(72) Inventors: Naiqian Zhi, Hartford, CT (US); Benjamin Wanamaker, Highland, UT (US); Rajiv Bhan, Hartford, CT (US); Sumeet Kumar, San Jose, CA (US)

(73) Assignee: Aetna Inc., Hartford, CT (US)

( * ) Notice: Subject to any disclaimer, the term of this patent is extended or adjusted under 35 U.S.C. 154(b) by 10 days.

(21) Appl. No.: 16/916,004

(22) Filed: Jun. 29, 2020

(65) Prior Publication Data

US 2021/0401295 A1 Dec. 30, 2021

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0022* (2013.01); *A61B 5/1118* (2013.01); *A61B 5/14551* (2013.01); *A61B 5/681* (2013.01); *A61B 5/7264* (2013.01); *G06F 16/24522* (2019.01); *G06N 3/04* (2013.01);
(Continued)

(58) Field of Classification Search
CPC ... A61B 5/0205; A61B 5/0022; A61B 5/1118; A61B 5/14551; A61B 5/681; A61B 5/7264; A61B 5/02438; G06F 16/24522; G06N 3/04; G06N 3/08; G16H 10/60; G16H 20/30; G16H 40/67; G16H 50/70
See application file for complete search history.

(56) References Cited

U.S. PATENT DOCUMENTS

2016/0302671 A1* 10/2016 Shariff ................. A61B 5/0205
2017/0132395 A1 5/2017 Futch
(Continued)

OTHER PUBLICATIONS

Mikolov et al., "Efficient Estimation of Word Representations in Vector Space," ICLR Workshop Papers (2013).
(Continued)

*Primary Examiner* — Tse W Chen
*Assistant Examiner* — Joseph A Tombers
(74) *Attorney, Agent, or Firm* — Leydig, Voit & Mayer, Ltd.

(57) ABSTRACT
A system and method are disclosed for monitoring health conditions based on data collected by a wearable device such as an activity tracker or a smart watch. Deep learning algorithms are configured to process an input vector that includes monitored parameter data collected by the wearable device as well as embedding data obtained from health records corresponding to a user account registered to the wearable device. In some embodiments, the input vector can also include social determinants data and/or demographic data. The output of the deep learning algorithms provides classifiers that represent probabilities that the user of the wearable device has an underlying health condition. If any underlying health condition is detected, then the user can be notified directly, via the wearable device or an associated application or technology, or indirectly, via a primary care provider associated with the user.

20 Claims, 8 Drawing Sheets

(51) Int. Cl.

| | |
|---|---|
| *A61B 5/11* | (2006.01) |
| *A61B 5/1455* | (2006.01) |
| *G06F 16/2452* | (2019.01) |
| *G06N 3/04* | (2023.01) |
| *G06N 3/08* | (2023.01) |
| *G16H 10/60* | (2018.01) |
| *G16H 20/30* | (2018.01) |
| *G16H 40/67* | (2018.01) |
| *A61B 5/024* | (2006.01) |

(52) U.S. Cl.

CPC .............. *G06N 3/08* (2013.01); *G16H 10/60* (2018.01); *G16H 20/30* (2018.01); *G16H 40/67* (2018.01); *A61B 5/02438* (2013.01)

(56) References Cited

U.S. PATENT DOCUMENTS

| | | | | |
|---|---|---|---|---|
| 2017/0242974 | A1* | 8/2017 | Zhao | .................... A61B 5/0245 |
| 2018/0211010 | A1* | 7/2018 | Malhotra | ............... G16H 50/30 |
| 2018/0232495 | A1 | 8/2018 | Li et al. | |
| 2019/0279647 | A1 | 9/2019 | Jones et al. | |
| 2019/0287685 | A1* | 9/2019 | Wu | ......................... G06F 40/30 |
| 2020/0075152 | A1 | 3/2020 | Radovcic | |
| 2020/0138360 | A1* | 5/2020 | Fan | .................... A61B 5/14551 |
| 2020/0185102 | A1* | 6/2020 | Leventhal | ................ G06N 5/04 |
| 2020/0202997 | A1 | 6/2020 | Hadad et al. | |
| 2021/0343384 | A1 | 11/2021 | Purushothaman et al. | |

OTHER PUBLICATIONS

International Patent Application No. PCT/US2021/039611, International Search Report (Oct. 18, 2021).

* cited by examiner

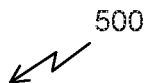

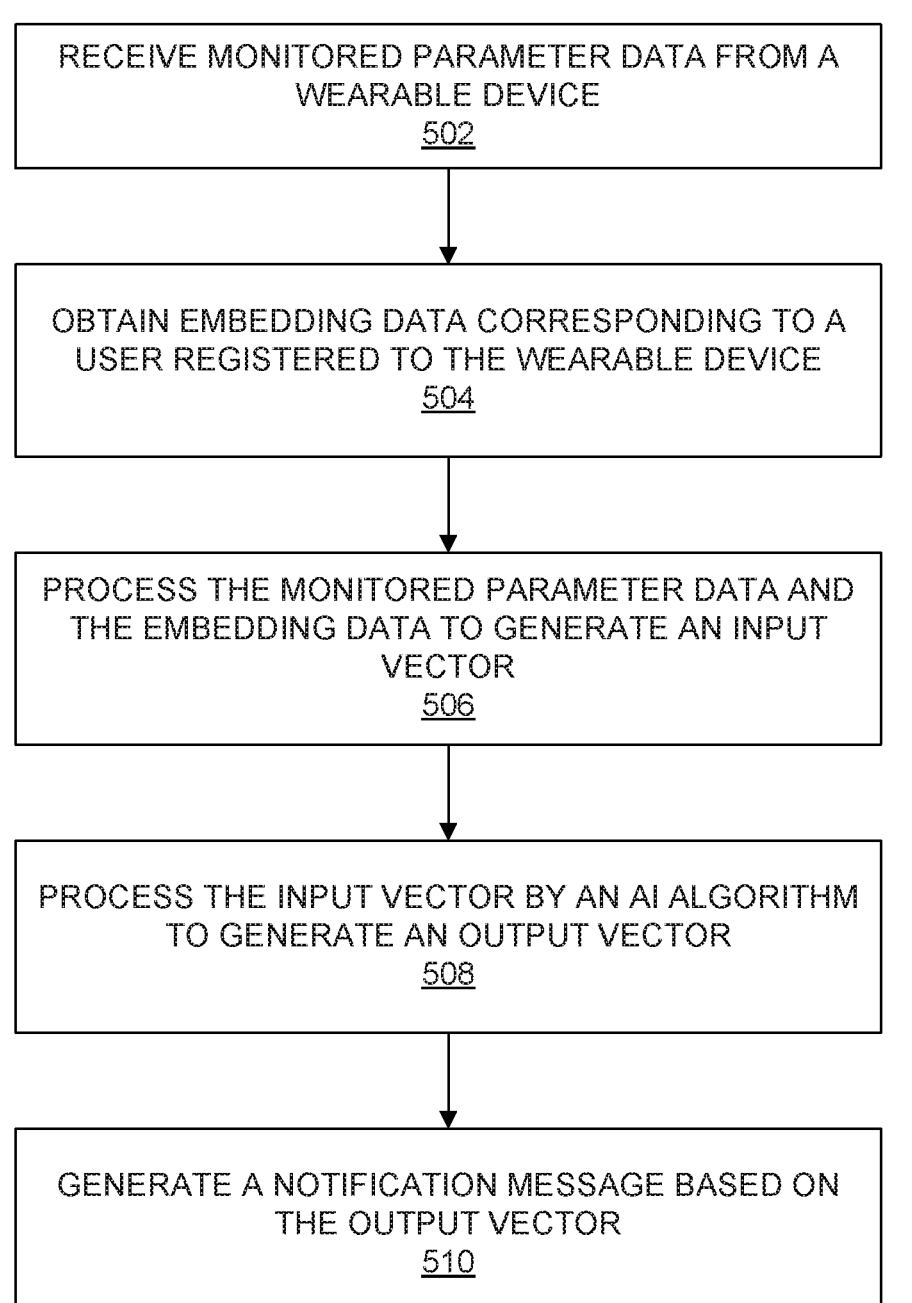

RECEIVE MONITORED PARAMETER DATA FROM A
WEARABLE DEVICE
502

OBTAIN EMBEDDING DATA CORRESPONDING TO A
USER REGISTERED TO THE WEARABLE DEVICE
504

PROCESS THE MONITORED PARAMETER DATA AND
THE EMBEDDING DATA TO GENERATE AN INPUT
VECTOR
506

PROCESS THE INPUT VECTOR BY AN AI ALGORITHM
TO GENERATE AN OUTPUT VECTOR
508

GENERATE A NOTIFICATION MESSAGE BASED ON
THE OUTPUT VECTOR
510

*Fig. 5*

SYSTEM AND METHODS UTILIZING ARTIFICIAL INTELLIGENCE ALGORITHMS TO ANALYZE WEARABLE ACTIVITY TRACKER DATA

TECHNICAL FIELD

The application relates to wearable activity trackers. More specifically, the application is directed to artificial intelligence algorithms configured to analyze wearable activity tracker data to assist with health monitoring.

BACKGROUND

Wearable health monitoring systems such as the features built into consumer devices like a Fitbit® device or an Apple® Watch, among others, or clinical devices like network connected blood glucose monitors are becoming more common. Consumers are tracking their steps (e.g., pedometer), heart rate (e.g., resting hear rate, peak heart rate, heart rate variability, etc.), oxygen level (e.g., VO2 Max), activity levels (e.g., calories, minutes of exercise, etc.), and the like using these devices, typically to encourage a more active and healthy lifestyle. This data generates thousands or millions of data points for a consumer, and some of this information can be highly correlated to the presence of certain diseases, oftentimes undiagnosed. However, this data is typically not shared with a patient's primary care physician or used in any clinical setting for medical diagnosis.

Some of the consumer companies have developed application programming interfaces (APIs) that allow this data to be shared with third parties, such as a clinician or a company offering health-based incentives such as discounts for those individuals that meet certain goals. In some cases, certain parameters like heart rate or VO2 max can be tracked over time and analyzed by artificial intelligence algorithms to attempt to detect certain health conditions. However, such algorithms are typically limited as they are not tailored to a specific user's physiology. The effectiveness of the artificial intelligence algorithm might not be sufficient for a user to rely on the output of said algorithm. Therefore, there is a need to improve the algorithms directed to use this wearable activity tracker data.

SUMMARY

A system and method for utilizing wearable device data to perform health monitoring are disclosed. Deep learning techniques are utilized to analyze monitored parameter data collected by a wearable device in conjunction with additional embedding data derived from health records or other sources. In particular, the techniques and systems described herein can be utilized by insurance providers or other sources of health record information to supplement the monitored parameter data collected by the wearable device.

In accordance with one aspect of the present disclosure, a system for performing health monitoring is disclosed. The system includes a server device including a memory and one or more processors. The one or more processors are configured to: receive monitored parameter data from a wearable device; obtain embedding data corresponding to a user registered to the wearable device; process the monitored parameter data and the embedding data to generate an input vector; process the input vector by an artificial intelligence algorithm to generate an output vector; and generate a notification message based on the output vector.

In some embodiments, the wearable device is an activity tracker. The monitored parameter data includes data points related to one or more of: a heart rate, an oxygen level, an activity level including at least one of a number of steps, a number of flights climbed, or a duration of exercise, or a number of calories burned. In an embodiment, the monitored parameter data further includes information logged by a user manually, where the information can include, but is not limited to, one of a height or a weight of the user.

In some embodiments, obtaining the embedding data comprises processing health records for a user via a natural language processing algorithm. The health records correspond to a registered user of the wearable device.

In some embodiments, the health records are stored in a database and comprise at least one of: claims records received from a health care provider, prescription records received from a pharmacy, or laboratory results received from a laboratory or other health care provider.

In some embodiments, the input vector data further includes social determinants data including one or more of: economic information, neighborhood information, education information, nutritional information, or environmental information. In some embodiments, the input vector data further includes demographic data including one or more of: age information, gender information, neighborhood type information (e.g., urban, suburban, rural, etc.), family size information, or employment indicator information.

In some embodiments, the artificial intelligence algorithm comprises one or more of: a multi-layer perceptron (MLP) algorithm, a convolution neural network (CNN), or a recurrent neural network (RNN).

In some embodiments, the notification message is transmitted to one of the wearable device or a mobile device associated with the wearable device to provide a user of the wearable device with a suggested action. In an embodiment, the suggested action includes information to facilitate scheduling an appointment with a healthcare provider.

In some embodiments, the notification message is transmitted to a healthcare provider to suggest treatment options that may be applicable to a patient.

In another aspect of the present disclosure, a method is disclosed for performing health monitoring. The method includes the steps of: receiving monitored parameter data from a wearable device, obtaining embedding data corresponding to a user registered to the wearable device, processing the monitored parameter data and the embedding data to generate an input vector, processing the input vector by an artificial intelligence algorithm to generate an output vector, and generating a notification message based on the output vector.

In yet another aspect of the present disclosure, a wearable device is disclosed. The wearable device includes a memory for storing data points associated with one or more monitored parameters, a transceiver for communicating with a server device over a network, and at least one processor. The at least one processor is configured to: sample one or more sensors to generate data points for each of the one or more monitored parameters, store the data points in the memory, transmit at least a portion of the data points to the server device, and receive a notification message from the server device. The notification message includes a suggested action identified based on the output of an artificial intelligence algorithm configured to process an input vector that includes the at least a portion of the data points for the one or more monitored parameters and embedding data corresponding to the wearable device.

In some embodiments, the wearable device comprises a wearable activity tracker.

BRIEF DESCRIPTION OF THE DRAWINGS

FIG. 5 is a flow diagram of a method for identifying undetected medical conditions based on monitored parameter data collected by a wearable device, in accordance with some embodiments.

DETAILED DESCRIPTION

Figure 1A:
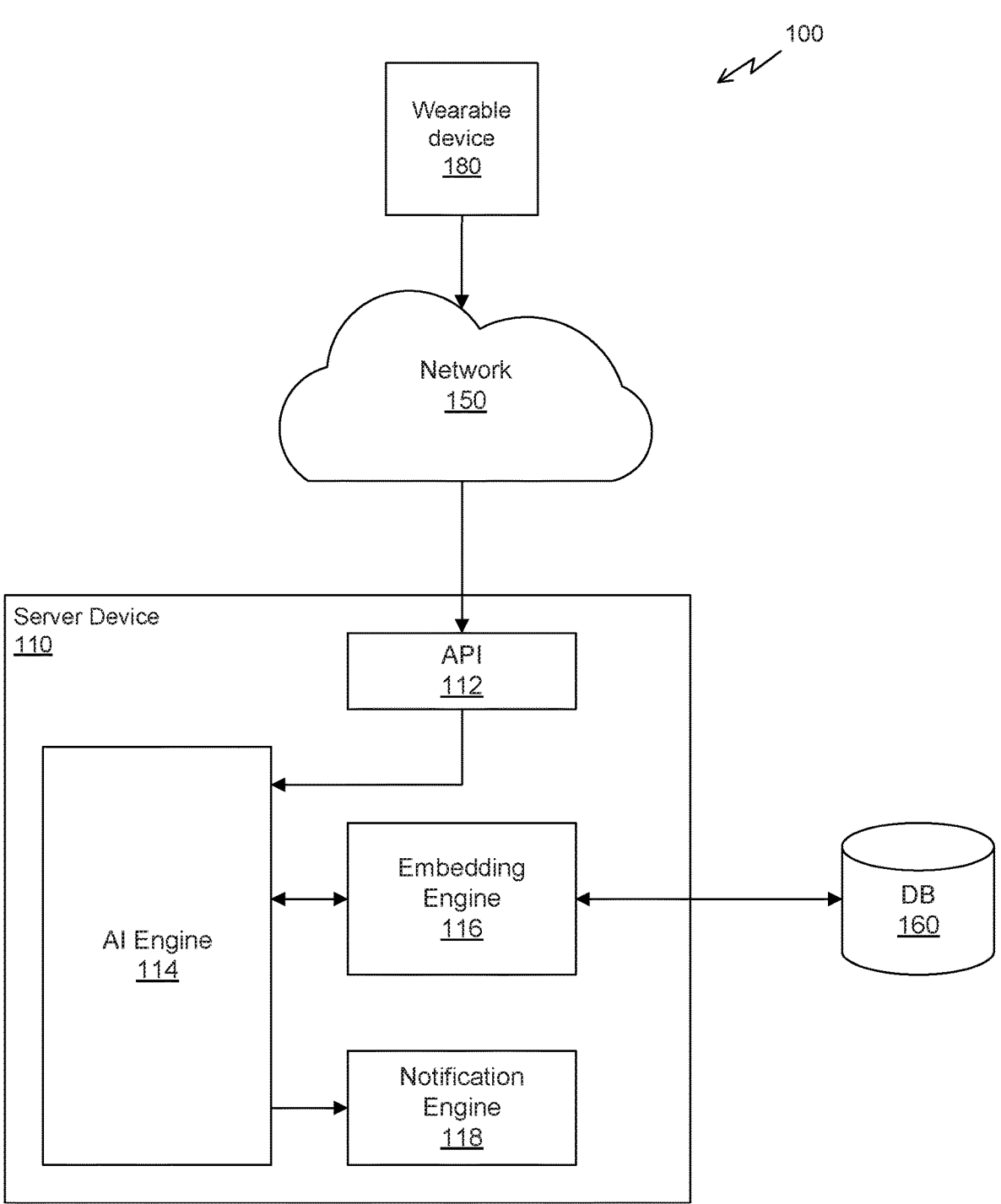
FIG. 1A illustrates a system for monitoring health conditions, in accordance with some embodiments.

Artificial Intelligence (AI) and Deep Learning Neural Networks (DLNN) can be utilized to assist in health monitoring techniques. A wearable device, such as a wearable activity tracker, oximeter, blood glucose monitor, or the like, can provide one or more monitored parameters to a server device. The monitored parameters can include, but are not limited to, a heart rate, heart rate variability, an electro cardiogram (ECG), a blood oxygen level, a duration of exercise, a number of steps, an altitude, exposure to environmental parameters (e.g., audio signals, air quality, temperature, etc.), menstruation cycles (e.g., basal body temperature, etc.), sleep cycles, acceleration (e.g., fall detection), and the like. The parameters can be logged automatically via sensor input or manually via user input, or any combination thereof. In some embodiments, the wearable device can be paired with other devices (e.g., blood glucose monitor, etc.) to collect parameter data. The monitored parameters can provide data points collected periodically, such as every second, minute, hour, or day. Different parameters can be collected at different frequencies. For example, a heart rate may be collected every minute whereas a heart rate variability can be collected daily (e.g., as derived from a plurality of heart rate data points collected throughout a 24 hour period).

A user registers the wearable device with a user account. The user account can be associated with additional data that can be used to supplement the monitored parameter data from the wearable device. For example, the additional data can include claims data for an insured person that is maintained by an insurance provider, which can include data collected from the insured person's primary care physician, clinical labs, pharmacies, or other health providers that submit claims information to the insurance provider for payment and/or processing. The claims data provides the insurance provider with additional insight into the health history of the patient that is useful for augmenting an artificial intelligence algorithm tasked with analyzing the information from the wearable device.

While the wearable device provides the AI algorithm with limited health information in a real-time or near real-time basis, the data is typically limited in scope and only provides insight into a small number of parameters related to a user's health. In contrast, the claims information may provide much more detailed insight into a specific user's physiology, but is typically collected on a much more limited basis (e.g., during once or twice a year appointments, when a person fills a prescription, when labs are run, etc.). By combining this data to provide a broad range of information to an AI algorithm, much more accurate assessments can be made by the AI algorithm, providing a user with more insight into potential health concerns before the person might otherwise be aware of the symptoms of such conditions. Experimental tests have seen 5-10% increases in accuracy of AI algorithms trained based on both monitored parameter data from a wearable device as well as additional embedding data from health records.

FIG. 1A illustrates a system 100 for monitoring health conditions, in accordance with some embodiments. As depicted in FIG. 1A, the system 100 includes a server device 110 connected to a network 150. The server device 110 comprises a memory and one or more processors configured to execute instructions. In an embodiment, the server device 110 is a blade server included in a chassis on a rack of a data center. In another embodiment, the server device 110 is a virtual machine that is run in the cloud. Although the components shown in the server device 110 can be executed by a single processor, in other embodiments, the server device 110 can refer to two or more server devices, each component included in the server device 110 executed by a particular one or more of the two or more server devices. For example, in an embodiment, the AI engine 114 can be executed on a second server device that is implemented in a public cloud such as Amazon® Web Services or Microsoft® Azure. The API 112, embedding engine 116, and/or notification engine 118 can be implemented on a private server device hosted in a data center operated by an insurance provider and can be configured to communicate with the AI engine 114 over a network. It will be understood that reference to a single server device 110 can include reference to multiple server devices.

In some embodiments, the server device 110 includes an application programming interface (API) 112, an artificial intelligence (AI) engine 114, an embedding engine 116, and a notification engine 118. The API 112 implements a set of algorithms to process API calls from a client. In an embodiment, the API 112 is configured to receive data packets that include the API calls from a wearable device 180. The API calls can include monitored parameter data collected by the wearable device 180. As used herein, the term "monitored parameter data" refers to one or more data points (e.g., samples) of each of one or more monitored parameters such as, but not limited to, a heart rate, heart rate variability, and ECG, an oxygen level, an activity level including at least one of a number of steps, a number of flights climbed, or a duration of exercise, a number of calories burned, a basal body temperature, a sleep duration, a blood glucose level, or the like. For example, the wearable device 180 can include light sensors that, when placed proximate a user's skin, are used to monitor a user's heart rate or blood oxygen level. As another example, the wearable device 180 can include a temperature sensor placed proximate the user's skin, that measures a surface temperature of the user's body at the location of the temperature sensor. The wearable device 180 collects one or more data points over a period of time such as a day or week, and then the wearable device 180 generates an API call including the data points and transmits the API call to the server device 110 via the network 150.

In some embodiments, the network 150 is a wide area network (WAN) such as the Internet. In other embodiments, the network 150 can be a radio access network such as a $4^{th}$ Generation (LTE, 4G) or Next Generation (5G) cellular network. In yet other embodiments, the network 150 can be a local area network (LAN) or a personal area network (PAN). The data packets can be Internet Protocol (IP) packets. It will be appreciated that any network, wired or wireless, can be utilized to transmit monitored parameter data to the server device 110 using any technically feasible protocols.

In some embodiments, the API 112 pre-processes the monitored parameter data received from the wearable device 180 and transmits the processed monitored parameter data to the AI engine 114. For example, the heart rate data can represent a number of data points, and the API 112 can be configured to derive average daily heart rate data from the monitored parameter data. In an embodiment, the API 112 can be configured to filter the monitored parameter data to select only a subset of parameters that are applicable for a given AI algorithm. For example, the monitored parameter data can include heart rate data, step information, calorie information, and oxygen level information. A particular AI algorithm may only call for heart rate data and oxygen level information and, therefore, the API 112 is configured to discard the step information and calorie information.

In some embodiments, the API 112 is configured to anonymize the monitored parameter data. Information related to a user's health is a privacy concern and, therefore, the API 112 can take steps to ensure any personally identifying information (PII) is removed before the monitored parameter data is forwarded to the AI engine 114. It will be appreciated that the API 112 may need to associate the monitored parameter data with a particular user or device, such as by using an identifier included in the API call or the header of a data packet to correlate the wearable device 180 with a particular user. The identifier can be a user identifier (ID) that is assigned to the wearable device 180 when the user registers the wearable device with a health monitoring service, or the identifier can be a network address, such as a media access control (MAC) address or an IP address of the wearable device 180. In some embodiments, the API 112 can use the identifier to allocate a task ID with the monitored parameter data such that the AI engine 114 or any other process that accesses the data cannot directly correlate the data with a particular user, user account, or user ID. In some cases, the monitored parameter data is also encrypted, either by the wearable device 180 or by the API 112.

In other embodiments, the API 112 stores the monitored parameter data in a memory or database, and sends a request message to the AI engine 114 that indicates the monitored parameter data is available at the memory or the database. It will be appreciated that the API 112 facilitates the collection of monitored parameter data from one or more wearable devices 180 associated with one or more distinct users or user accounts and provides the AI engine 114 with the monitored parameter data for processing.

In some embodiments, the AI engine 114 is configured to process inputs with one or more AI algorithms. The AI algorithms can include, but are not limited to, a multi-layer perceptron (MLP) algorithm, a convolution neural network (CNN), or a recurrent neural network (RNN). The AI algorithm uses the monitored parameter data to generate outputs that represent predictions related to the health of a user. For example, a CNN may be utilized to process an input vector including a number of data points that represent a heart rate variability for a user over a number of days (e.g., 7 days, 30 days, etc.). The heart rate variability data can be shown to be indicative of certain underlying health conditions such as hypertension, hyperlipidemia, sleep apnea, diabetes, and cardiovascular disease. The use of certain monitored parameter data collected from a wearable device and analyzed by deep learning models may be useful in helping to diagnose people with undetected conditions, but the accuracy of such models is not perfect because each individual has a unique physiology and environment. The heart rate of a young healthy individual with low body fat when compared against the heart rate of an older obese individual can be very different, even though the young person may be diabetic and the older person may not have any detected condition. Therefore, the AI algorithms can be improved by augmenting the monitored parameter data collected by the wearable device with additional information related to the user.

In an embodiment, the AI engine 114, upon receiving the monitored parameter data from the API 112, generates a request that is transmitted to the embedding engine 116. The request can include an identifier associated with the wearable device 180. The embedding engine 116 is configured to collect health records or other information from one or more data stores such as a database 160. For example, a health insurance provider can receive claims data from a variety of health care providers. The claims data is stored in a database 160 and used to process insurance claims. However, the embedding engine 116 can query the database 160 for any health records related to a user using the identifier included in the request. Thus, the embedding engine 116 collects additional information from one or more sources that is not available to the wearable device 180.

In some embodiments, the embedding engine 116 is configured to collect the additional information that is combined with the monitored parameter data from the wearable device 180 to increase the information provided as an input to the AI algorithm. In one example, a health insurance provider receives data related to a user's health as well as general demographic information and/or social determinants information. The data can include claims records received from a health provider, prescription records received from a pharmacy, or laboratory results received from a laboratory or other health care provider. The claims information may contain information about specific medical procedures undergone by the user in the past. The laboratory results can contain detailed information related to a user's comprehensive metabolic panels, for example. The prescription records can include information about the types of medications taken by a user. All of this information can provide a more comprehensive picture of the user's health condition than could be provided by the monitored parameter data alone.

In an embodiment, the embedding engine 116 is configured to process health records for a user via a natural language processing algorithm. Again, the health records correspond to a registered user of the wearable device. It will be appreciated that the health records that are retrieved from the database 160 can have a variety of formats. For example, a claims record may include a set of fields, each field including different information such as a member identifier, insurance product information, medical codes (e.g., ICD9 diagnostic codes), and the like. The job of the embedding engine 116 is to take a number of different natural language or standardized format health records and generate a vector of dimensionless features (e.g., 100 features) that indicates a user's health history over a specified time period. For example, a particular dimension can represent a particular combination of medical codes found throughout the user's health records. This feature vector, generated by a natural language processing algorithm such as Word2vec described in Mikolov et al., "Efficient Estimation of Word Representations in Vector Space," ICLR Workshop Papers, 2013, which is herein incorporated in its entirety, or the like, represents the additional data that is combined with the monitored parameter data.

For example, a member's health history includes a sequence of medical codes including ICD (International Statistical Classification of Diseases) 9/10 diagnostic codes, CPT (Current Procedural Terminology) procedure codes, GPI (Generic Product Identifier) drug codes, and LOINC (Logical Observation Identifiers Names and Codes) lab codes. The embedding engine 116 includes a 100-dimensional lookup matrix that is trained based on health histories of millions of members collected over a number of years. The health history of a particular member can be parsed to extract the codes set forth above, to generate a list of codes included in that member's health history. Each code is then processed by the lookup matrix to generate a corresponding 100-dimensional vector and the average of the vectors for the set of codes generated from the member's health history is provided as the embedding data.

In some embodiments, the embedding data is combined with additional data such as demographic data (e.g., age, race, gender, etc.) or social determinants data, described in more detail below. When combined with the monitored parameter data, this information provides a more comprehensive view of the user's health that can be processed by the AI algorithm.

The AI engine 114 processes the input vector via one or more AI algorithms. In some embodiments, the AI engine 114 can generate separate input vectors for each AI algorithm, according to the requirements of the AI algorithm. For example, one type of algorithm can be better for diagnosing a medical condition such as hypertension while a different type of algorithm can be better for diagnosing a medical condition such as sleep apnea. The output vector from each of the one or more AI algorithms can represent classifiers associated with different medical conditions. A classifier can be a scalar value between 0 and 1 that represents a probability that the user may have the underlying health condition associated with that classifier.

Once the output vector(s) are generated, the AI engine 114 may compare each classifier to a threshold value. If the classifier is above a threshold value, then the user may have a high likelihood of having the underlying health condition. In such cases, the AI engine 114 can transmit a request to the notification engine to notify the user about the detected health condition.

In an embodiment, the notification engine 118 can generate a notification message that is transmitted to the wearable device 180 to provide a user of the wearable device with a suggested action. For example, the suggested action can include information to facilitate scheduling an appointment with a healthcare provider. In another embodiment, the notification message is transmitted to a healthcare provider to suggest treatment options that may be applicable to a patient (e.g., the user).

Figure 1B:
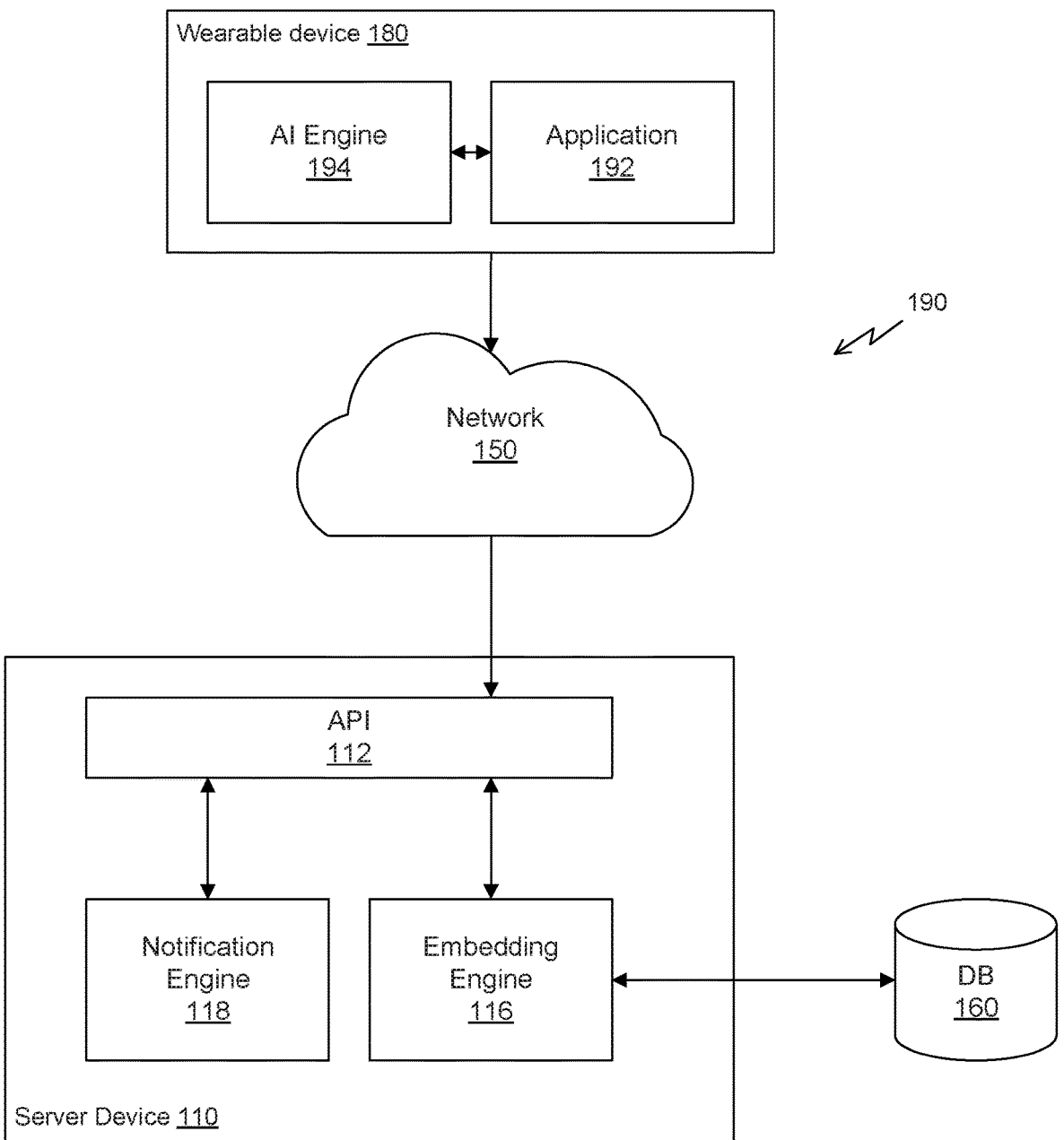
FIG. 1B illustrates a system for monitoring health conditions, in accordance with other embodiments.

FIG. 1B illustrates a system 100 for monitoring health conditions, in accordance with other embodiments. As depicted in FIG. 1B, the wearable device 180 includes and application 192 configured to collect data points on one or more parameters monitored by the wearable device 180. In addition, the wearable device 180 also includes the AI engine 194, which is similar to AI engine 114 but is executed locally on the wearable device 180. Rather than transmitting the parameter data collected by the wearable device 180 to the sever device 110, the application 192 can request the server device 110 to transmit embedding data generated by the embedding engine 116 to the application 192, which combines the embedding data with the monitored parameter data stored on the wearable device 180. The combined data is then processed by the AI engine 114 to generate the output vector(s) as described above.

It will be appreciated that the system 190 may be more secure than the system 100 as the monitored parameter data is not transmitted over the network 150, and the embedding data transmitted over the network 150 is merely a vector that represents a user's health history and is not easily translated into the original health history information stored in the database 160. However, the system 190 may require more computing capacity in the wearable device 180 in order to execute the AI algorithm(s).

In some embodiments, the functionality of the wearable device 180 can be split between a wearable activity tracker with limited processing capacity and a mobile device, such as a cellular phone or tablet computer. The mobile device can be connected to the network 150 and the wearable activity tracker can be connected to the mobile device. An application on the mobile device collects monitored parameter data from the wearable activity tracker and transmits the monitored parameter data to the server device 110 to be processed by the AI engine 114, as in system 100, or receives embedding data from the server device 110 to be processed by the AI engine 194, as in system 190. In other embodiments, the mobile device can be used to provide the wearable device 180 with at least some monitored parameter data. For example, a user can use the mobile device to provide manually logged data related to one or more monitored parameters that are sent to the wearable activity tracker for processing. In such embodiments, the mobile device can provide additional user interfaces for the wearable activity tracker, but the wearable activity tracker maintains the functionality for processing the monitored parameter data.

Figure 2A:
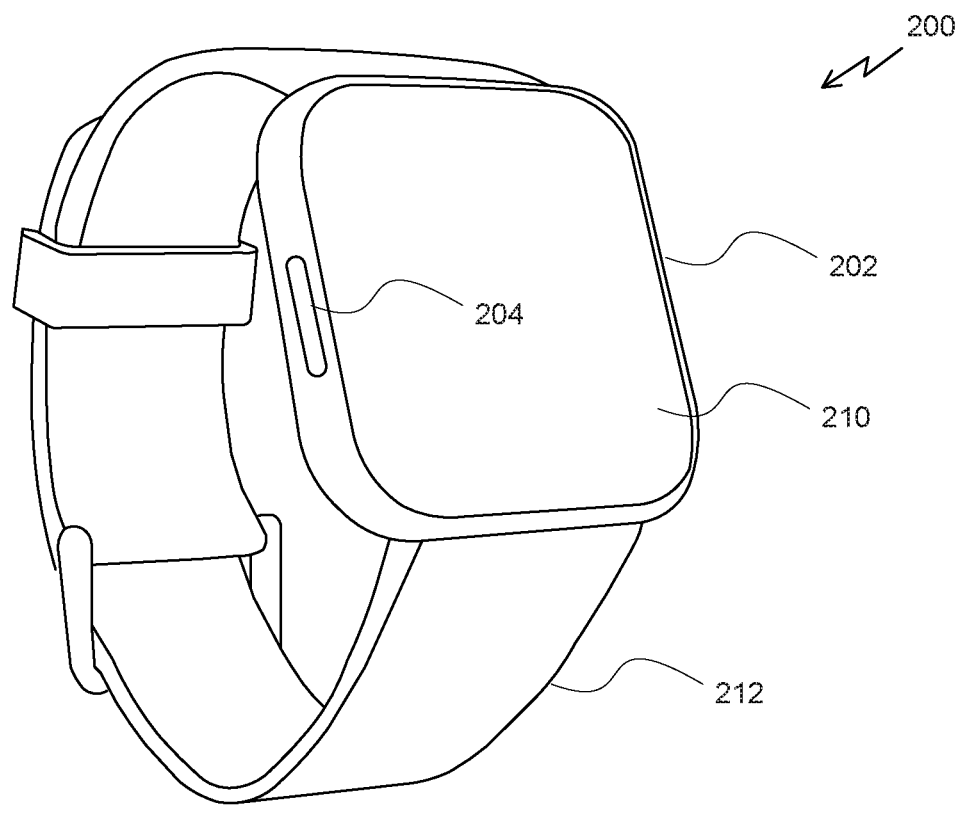
FIGS. 2A & 2B illustrate a wearable device, in accordance with some embodiments.
Figure 2B:
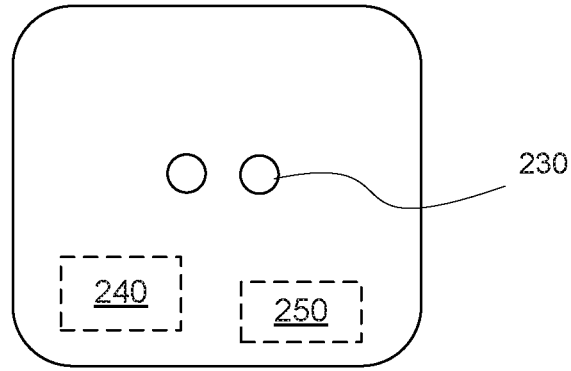

FIGS. 2A & 2B illustrate a wearable device 200, in accordance with some embodiments. The wearable device 200 is a watch that includes sensors for collecting data points on one or more parameters related to the health of a user. As shown in FIG. 2A, the wearable device 200 includes a body 202 that houses electronics including a processor, a memory, a transceiver, an antenna, a battery, and the like. The wearable device 200 also includes a button 204, a display 210, and a band 212. The display 210 is a liquid crystal display (LCD), an organic light emitting display (OLED), or the like. The display 210 is configured to display information to a user and can include a touch function that enables the user to enter information using the wearable device. The display 210 can display information such as a time or date, notifications such as alarms or indications of a text message or phone call, and information related to collected information such as a number of steps counted in a day using a pedometer function or a current heart rate of the user, among other information.

As shown in FIG. 2B, the back of the body 202 can include sensors 230 for collecting monitored parameter data. For example, the sensors 230 can include a light emitting diode that produces a light and a light sensor that detects lights (e.g., optical pulse sensors). The light emitted from the light emitting diode can enter the user's skin and the signal detected by the light sensor can be used to monitor, for example, a user's heart rate or blood oxygen level. The sensors 230 can include other types of sensors such as capacitive sensors, moisture sensors, image sensors, electrooculogram (EOG) or electroretinogram (ERG) sensors, respiration sensors, airflow sensors, temperature sensors, and the like. The scope of the present disclosure is not limited to a specific type of sensor and any sensor capable of collecting any kind of health information about a user is contemplated as being included in the wearable device 200.

As depicted in FIG. 2B, the wearable device 200 includes a processor 240 and a transceiver 250. In some embodiments, the processor 240 is a system on chip (SoC) and is configured to execute one or more processes that collect monitored parameter data using the sensors 230 and transmit the monitored parameter data to the server device 110 via the transceiver. In one embodiment, the wearable device 200 is configured to transmit the monitored parameter data to an access point connected to a network using Wi-Fi or some other wireless technology.

It will be appreciated that the wearable device 200 shown in FIGS. 2A & 2B is only one exemplary device and that other types of wearable devices are contemplated as being within the scope of this disclosure. For example, the wearable device 200 could be a clinical medical device such as a blood glucose monitor or a wearable electrocardiogram (ECG) monitor, smart glasses that include augmented reality and/or virtual reality capabilities, smart rings, bracelets, headbands, hearing aids, or any other devices worn by a user that include one or more sensors for monitoring some parameter related to the user. In some embodiments, the wearable device is a smart phone that includes a fitness application that tracks, e.g., an activity level of a user.

Figure 3:
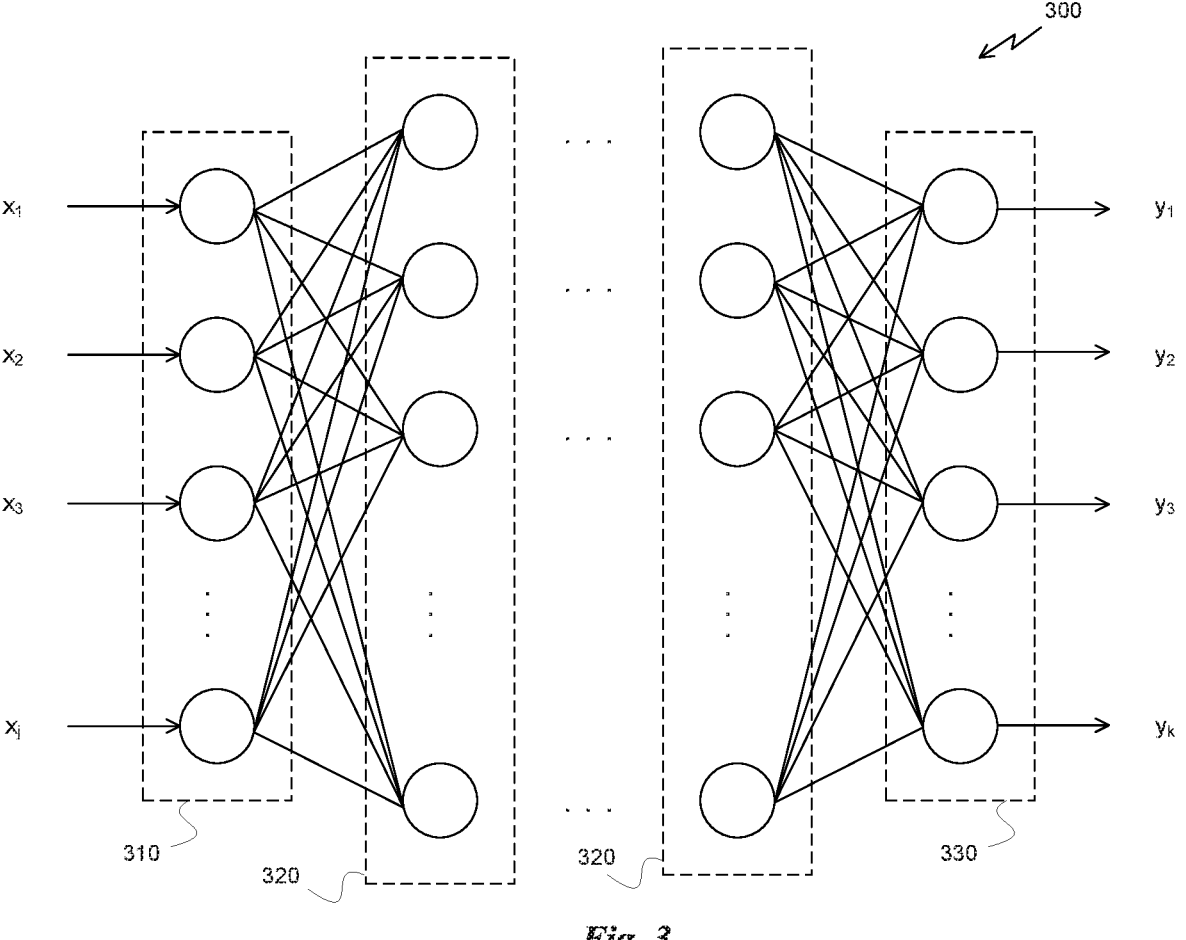
FIG. 3 is an artificial intelligence algorithm, in accordance with some embodiments.

FIG. 3 is an artificial intelligence algorithm 300, in accordance with some embodiments. The AI algorithm 300 is a multi-layer perceptron (MLP) algorithm. The MLP is a neural network that includes a plurality of artificial neurons arranged in a series of layers. As depicted in FIG. 3, the MLP includes an input layer 310, one or more hidden layers 320, and an output layer 330. Each artificial neuron within a layer is connected to one or more artificial neurons in a subsequent layer, but no artificial neuron in a particular layer is connected to another artificial neuron in the particular layer.

An input vector, $\{x_1, x_2, \ldots, x_j\}$, is provided as inputs to the input layer 310, where each element of the input vector is coupled to one of the artificial neurons in the input layer 310. Each artificial neuron applies a linear transformation and, optionally, a nonlinear transformation to the inputs connected to the artificial neuron. In the linear transformation, a weight can be applied to each of one or more inputs attached to the artificial neuron and then the weighted inputs can be summed to produce an intermediate output signal. In the nonlinear transformation, the intermediate output signal can be processed by an activation function such as a Sigmoid function or a Rectified Linear Unit (ReLU) to produce an activation signal of the artificial neuron. The activation signal can be fanned out to one or more artificial neurons in the subsequent layer.

The input layer 310 is followed by one or more hidden layers 320. The number of artificial neurons in the hidden layer 320 does not have to match the number of artificial neurons in the input layer 310. In some embodiments, each hidden layer is fully connected, meaning that each artificial neuron in the hidden layer receives all of the activation signals generated by the set of artificial neurons in the previous layer (e.g., the input layer or a preceding hidden layer). In other embodiments, each artificial neuron in the hidden layer receives only a subset of activation signals generated by the set of artificial neurons in the previous layer.

The output layer 330 follows the last hidden layer 320 and generates an output vector, $\{y_1, y_2, \ldots, y_k\}$. It will be appreciated that the dimension j of the input vector can be independent of the dimension k of the output vector. In an embodiment, each element of the output vector represents a probability of a person associated with the input vector having a particular underlying medical condition.

In an embodiment, the input vector is composed of a first portion corresponding to monitored parameter data from a wearable device 180 and a second portion corresponding to embedding data associated with a user registered to the wearable device 180. In some embodiments, the input vector can also include additional information such as demographic data and/or social determinants data, as discussed in more detail below.

It will be appreciated that the AI algorithm 300 is trained using a training data set. In an embodiment, a health insurance company collects data related to a large number of insured individuals. The data can include both health records and monitored parameter data from wearable devices. The health records provide insight on subpopulations in the number of insured individuals that have been diagnosed with one of a variety of medical conditions. The health records can be analyzed to create a ground-truth output vector for each individual. The health records and monitored parameter data collected from a wearable device registered to that individual can be used to generate an input vector that corresponds to the ground-truth output vector. Pairs of input vectors and ground-truth output vectors can then be stored in a database for a large number of insured individuals to generate the training data set.

In order to train the AI algorithm 300, various parameters of the AI algorithm 300 are initialized. In an embodiment, each artificial neuron is associated with a set of weights corresponding to the inputs connected to the artificial neuron. Each weight can be initialized to a random or pseudo-random value (e.g., each weight can be set between 0 and 1, or −1 and 1). In some embodiments, each artificial neuron can also be associated with a bias value. Once the parameters of the AI algorithm 300 are initialized, each input vector in the training data set is processed by the AI algorithm 300 to generate an output vector. The output vector is compared to the ground-truth output vector for that individual based on a cost function, and the parameters of the AI algorithm 300 are adjusted using known techniques, such as back propagation with gradient descent, in order to minimize the cost function. The cost function can be an L1 cost function such as a sum of absolute differences (SAD) or an L2 cost function such as a sum of square differences (SSD).

Once the AI algorithm 300 is trained, the AI algorithm 300 can be employed with new user data. As monitored parameter data is received from a wearable device 180, the input vector can be generated, including the corresponding embedding data, and processed to generate an output vector. The output vector classifies the probability that the user may have one of a plurality of undiagnosed medical conditions.

As described above, the MLP is only one type of AI algorithm 300 that can be implemented by the AI engine 114. The MLP is applied to a one dimensional input vector having a number of elements. In contrast, other AI algorithms 300 can be implemented that analyze a two dimensional input vector.

Figure 4:
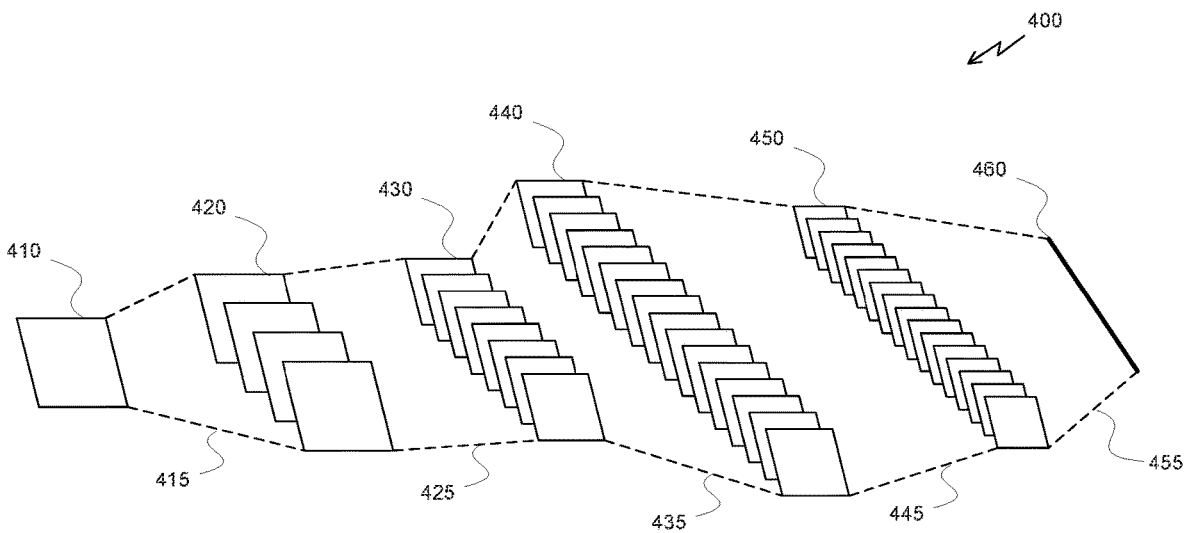
FIG. 4 illustrates a convolution neural network (CNN), in accordance with some embodiments.

FIG. 4 illustrates a convolution neural network (CNN) 400, in accordance with some embodiments. A CNN is typically used in applications such as image classification or image processing. The convolution operation applies a moving filter, referred to as a convolution kernel, across the input image to generate a set of feature maps. Each layer of the CNN further refines the set of feature maps through subsequent convolution operations and downsampling in order to generate a large number of features that are significantly reduced in spatial resolution. A fully connected layer then combines these features to generate an output vector. In some embodiments, CNNs can be implemented as U-nets, which include an encoder portion that generates the set of features and a decoder portion which performs deconvolution operations and upsampling to generate a processed image from the set of features generate by the encoder portion.

As depicted in FIG. 4, an input vector 410 is a two-dimensional matrix. A first portion of the matrix comprises monitored parameter data. A second portion of the matrix comprises embedding data. In some embodiments, the matrix can also include demographic data and/or social determinants data. In some embodiments, the input vector is a plurality of channels, each channel including a two dimensional matrix. A first channel includes the monitored parameter data, a second channel includes the embedding data, and, optionally, a third channel and/or a fourth channel includes demographic data and social determinants data, respectively.

A first layer 415 of the CNN 400 performs a two dimensional convolution operation on the input vector 410 to generate a set of feature maps 420. The number of channels of the feature maps can be more than the number of channels of the input vector 410. For example, each channel of the feature maps 420 can correspond to a different convolution kernel applied to a particular channel of the input vector 410.

A second layer 425 is a downsampling layer that generates a second set of feature maps 430 from the set of feature maps 420. The downsampling operation can be implemented by a pooling layer or, less typically, a convolution operation with a stride greater than one element. A stride refers to moving the convolution filter by more than one element each time the convolution filter is applied to the input feature map. For example, a stride of 2×2 means that the convolution filter is applied to every other element of the feature map such that the output feature map is half the resolution of the input feature map in each dimension. A pooling layer, on the other hand, is applied to a subset of elements (e.g., each 2×2 set of elements) and selects, either, a maximum value in the subset, a mean value in the subset, or a minimum value in the subset as the output for a corresponding element in the output feature map. It will be appreciated that the number of channels in the feature maps output by a pooling layer is typically the same as the number of channels in the feature maps input to the pooling layer. However, where subsampling is implemented using convolution operations with strides greater than one in either dimension, the number of channels in the feature maps can increase.

The CNN 400 can include additional layers such as a convolution layer 435 and a subsampling layer 445 that generate sets of feature maps 440 and 450, respectively. Although not shown explicitly, a large number of layers can be included in the CNN 400. Examples of deep neural networks can include more than 50 or 100 layers. Furthermore, although not shown explicitly, the CNN 400 can also include activation layers, which apply an activation function to each of the elements of the feature maps. Again, examples of common activation functions are ReLU and Sigmoid.

The final layer 455 is a fully connected layer that processed the set of feature maps 450 to generate an output vector 460. In one embodiment, the output vector 460 is a one-dimensional vector that classifies the probability of an individual to have each of a plurality of undetected medical conditions. In other embodiments, the output vector 460 can be a two-dimensional matrix.

It will be appreciated that the AI algorithm is not limited to the MLP or the CNN implementations described above. In another embodiment, the AI algorithm is a recurrent neural network (RNN). In an embodiment, the RNN is implemented similar to the MLP of FIG. 3, except each neural network maintains a state h that can affect the activation level of the artificial neuron. Essentially, a recurrent neural network is similar to the MLP except that the past state of each neuron is not returned to a base state before processing a new input vector. In another embodiment, the RNN is implemented similar to the CNN of FIG. 4, where the fully connected layer 455 is replaced with one or more recurrent layers (e.g., bidirectional layers) that maintain a state h.

Other types of AI algorithms are also within the scope of the present disclosure. These algorithms can include residual neural networks, regression algorithms, and the like. The particular type of AI algorithm that is implemented can depend on the particular application and may consider the particular type of monitored parameter data received from a wearable device 180.

FIG. 5 is a flow diagram of a method 500 for identifying undetected medical conditions based on monitored parameter data collected by a wearable device, in accordance with some embodiments. The method 500 can be performed by a program, custom circuitry, or by a combination of custom circuitry and a program. Furthermore, persons of ordinary skill in the art will understand that any system that performs method 500 is within the scope and spirit of the embodiments described herein.

At step 502, monitored parameter data is received from a wearable device. In an embodiment, a server device 110 receives the monitored parameter data from a wearable device 180 via a network 150. The monitored parameter data can include data points (e.g., samples) for one or more monitored parameters that can include at least one of: a heart rate; an oxygen level, an activity level including at least one of a number of steps, a number of flights climbed, or a duration of exercise, or a number of calories burned. In some embodiments, the monitored parameter data is collected automatically using sensors included in the wearable device 180. In some embodiments, the monitored parameter data can include manual logged data that is manually entered into the wearable device 180 by a user. Manual logged data can include characteristics such as a height or weight of a user, exercise activity (e.g., a number of minutes for the duration of exercise, a type of exercise, etc.), and the like. In some cases, these characteristics can be automatically logged by the wearable device using sensors or interfaces between the wearable device and other health or fitness equipment. For example, a wearable tracker can establish a communication channel with a smart scale that enables the user's weight to automatically be logged by the wearable tracker every time the user steps on the scale. As another example, the wearable tracker can include inertial sensors that enable the tracker to determine motion consistent with exercise activity and log the number of minutes that the activity is performed.

At step 504, embedding data is obtained corresponding to a user registered to the wearable device. In an embodiment, a user registers the wearable device with a user account. The user account can correspond to a product or service offered by a service provider such as, for example, a user account for an insured individual that is enrolled in an insurance product offered by an insurance provider. In some embodiments, the embedding data is obtained by retrieving health records corresponding to the user registered to the wearable device 180. Obtaining the embedding data can include processing one or more health records for a user via a natural language processing algorithm. The output of the natural language processing algorithm can be a feature vector including a number of features (e.g., scalar values).

At step 506, the monitored parameter data and the embedding data are processed to generate an input vector. In an embodiment, the monitored parameter data from the wearable device 180 and the embedding data obtained or derived from the health records is combined to generate an input vector for an AI algorithm. In an embodiment, only a subset of the monitored parameter data is selected to be included in the input vector. For example, data points can be selected corresponding to a specific time period (e.g., the most recent 6 months). As another example, only data points for a select number of monitored parameters (e.g., heart rate variability) are included in the input vector. In some embodiments, the data points are processed to generate derived data based on the monitored parameter data. For example, raw heart rate data can be processed to determine a maximum daily heart rate for each day over the last 6 months. Similarly, the embedding data can also be processed to select a subset of the embedding data to include in the input vector.

It will be appreciated that, in some cases, the health records for a user or the data points returned by the wearable device 180 may be sparse. For example, the user may not visit a primary care physician very often or the user may forget to use the wearable device 180 on some days. In some embodiments, where data is missing, the input vector may be populated with zero values to substitute for missing elements of the input vector. In other embodiments, the input vector may populate missing elements with mean values for a population, a last logged value prior to the missing data, or imputed values. For example, where a heart rate is missing for specific days, the input vector can be populated with a mean heart rate for a population or a subpopulation of users that matches the demographics of the particular user. The particular choice of how to populate the input vector for missing values due to sparse data is a design choice that can depend on the type of data that is missing and/or the specific AI algorithm selected to process the input vector.

In some embodiments, the input vector may also include additional information related to the user registered to the wearable device. In an embodiment, demographic information for the user can be included in the input vector. The demographic information, such as age, race, gender, or the like, can affect the classifiers output by the algorithm where certain diseases disproportionately affect different demographic populations. In another embodiment, social determinants data can be included in the input vector. Social determinants data can include economic information, neighborhood information, education information, nutritional information, or other types of environmental information. Examples of economic information can include employment data, income, expenses, debts, average medical bills, or the like. Examples of neighborhood information can include zip code/geography based on address of residence, types of housing, neighborhood characteristics (e.g., number of parks, schools, average income, etc.). Examples of education information can include level of schooling completed, literacy, primary language, number of languages, and the like. Examples of nutritional information can include measures related to access to food, dietary intake, food availability, and the like. Examples of environmental information can include stress, proximity to family (e.g., caregivers), access to healthcare, and the like.

The social determinants data can have a significant impact on health outcomes, but such information is rarely included in conventional health records or tracked by a wearable device 180. In some embodiments, the user will provide this information during interactions with the service provider. For example, when opening an account with the service provider, the user may fill in a form that provides at least some of the aforementioned social determinants data. In other embodiments, the social determinants data can be derived based on other information. For example, by receiving the user's address of residence, many characteristics related to the locality surrounding the address may be known. For example, databases can be built that indicate, by zip code, the type or number of parks and schools in an area, the average income in a given zip code, the location or number of health care providers in a certain area, and the like. Such generic information can be imputed on a user if specific information is not provided voluntarily.

In other instances, information related to a user can be derived from third-parties. For example, a user's credit history may provide information related to a user's financial stability and debts. Alternatively, the user may subscribe to other third-party service providers that collect information that the user has opted-in and allowed to be shared with the service provider. For example, a service provider that helps a user lose weight by tracking meals may share information related to the user's diet with the service provider. In some cases, such information has privacy concerns and, therefore, an opt-in by the user to share such information with the service provider may be required before such information can be retrieved from a third-party.

At step 508, the input vector is processed by the AI algorithm to generate an output vector. In some embodiments, the AI algorithm is a MLP. In other embodiments, the AI algorithm is a CNN or an RNN. In an embodiment, the AI algorithm generates an output vector that includes a plurality of classifiers, each classifier is a scalar value that represents a probability that the user has an underlying medical condition that may be undetected.

At step 510, a notification message is generated based on the output vector. In an embodiment, each of the classifiers is compared against a threshold value. If the classifier is above the threshold value, then that may indicate a high likelihood that the user has a medical condition corresponding to that classifier. The notification message can be sent to the user or a health care provider designated by the user to inform the user of the possibility of the medical condition.

In an embodiment, the notification message is transmitted to the wearable device to provide a user of the wearable device with a suggested action. The notification message can comprise a short message service (SMS) message, otherwise referred to as a text message, an application push notification, a message within an application transmitted according to an API, an email, or the like. In one embodiment, the text message can inform the user about the detection of an underlying medical condition. In another embodiment, the suggested action includes information to facilitate scheduling an appointment with a healthcare provider. For example, when a new medical condition is detected, the text message can suggest that the user schedule an appointment with the user's primary care provider and include a link to the primary care provider's website, a listing of the primary care provider's physical address, or a phone number to the primary care provider's office.

In another embodiment, the notification message is transmitted to a health care provider to suggest treatment options that may be applicable to a patient. Given the underlying medical condition, the health care provider can contact the patient and suggest treatment options or ask the patient to schedule an appointment. For certain conditions, it may be preferred to have a trained medical professional (e.g., a doctor, nurse, therapist, psychologist, etc.) or a trained call representative call the patient to inform them about the potential diagnosis in order to answer any questions the patient might have concerning such diagnosis or the method for diagnosing the patient based on the monitored parameter data, or to coordinate condition management by scheduling an appointment or the like with a medical professional.

Figure 6:
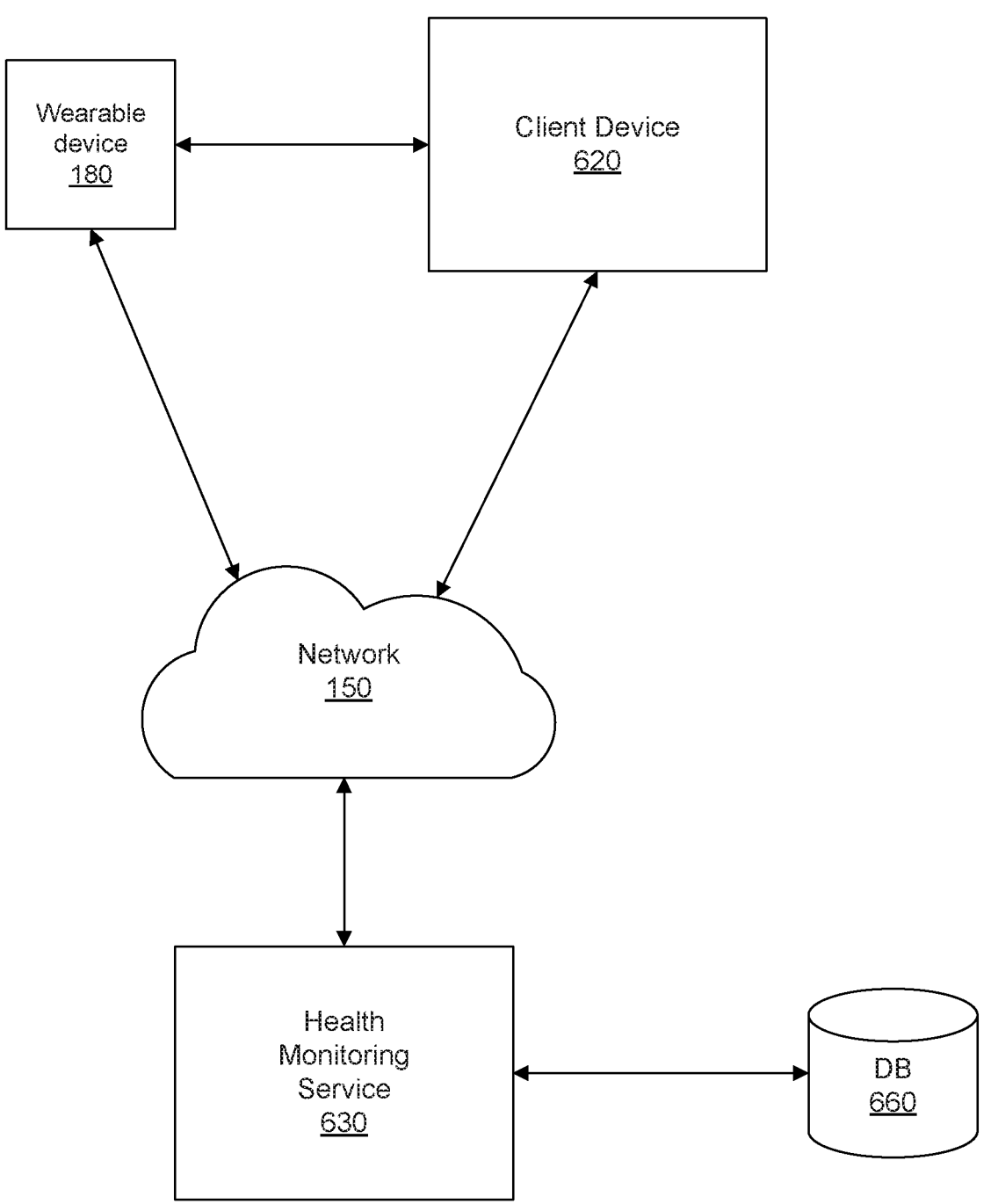
FIG. 6 is a conceptual illustration of a health monitoring service for identifying medical conditions based on monitored parameter data collected by a wearable device, in accordance with some embodiments.

FIG. 6 is a conceptual illustration of a health monitoring service 630 for identifying medical conditions based on monitored parameter data collected by a wearable device 180, in accordance with some embodiments. When a user obtains a wearable device 180, the user can opt-in to use a health monitoring service 630 offered by a service provider. In an embodiment, the user, through a client device 610, can access a web page using a web browser or other application executed by the client device 610. In an embodiment, the web page is a portal for an insurance provider and the user is prompted to log into a user account using credentials established by the user for a user account. Once logged in, the user may select an option provided through the web page to register a wearable device with the account and opt-in to a health monitoring service 630.

In one embodiment, the user provides information to identify the wearable device to the health monitoring service 630. For example, the user can enter a MAC address of the wearable device in a form element provided on the webpage. In another example, the health monitoring service 630 can prompt the user to download an application on the wearable device, where the application is configured to communicate directly with the health monitoring service 630. Once the application is running on the wearable device 630, the user can enter credentials for the user account in the application on the wearable device 180 or, alternatively, the user can be provided with a temporary code at the client device 610, which the user can then enter in the application on the wearable device 180. The temporary code is then transmitted from the wearable device 180 to the health monitoring service 630, which can then associate an identifier corresponding to the wearable device 180 with the user account based on the temporary code.

The example embodiments described above are merely a few of the many possible ways to register the wearable device 180 to the user account for the user. Any means for registering the wearable device 180 to the user account is contemplated as being within the scope of the present disclosure. Once the wearable device 180 is registered to the user account, such as by mapping a user account identifier to an identifier for the wearable device 180 in a database 660, the monitored parameter data received from the wearable device 180 can be associated with health records corresponding to the user account in order to generate the embedding data utilized, at least in part, by the AI algorithm.

Figure 7:
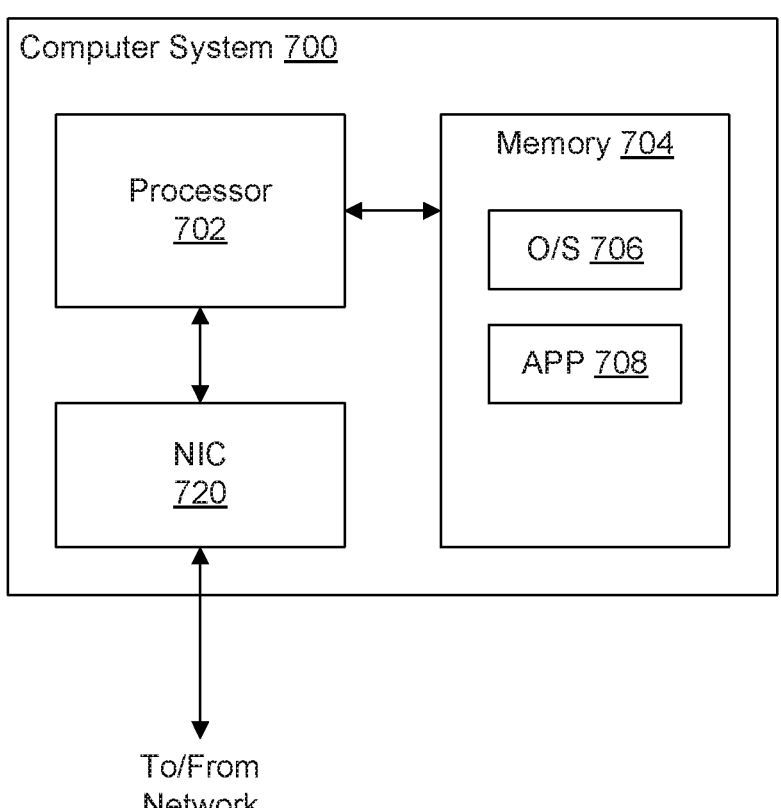
FIG. 7 illustrates an exemplary computer system, in accordance with some embodiments.

FIG. 7 illustrates an exemplary computer system 700, in accordance with some embodiments. The computer system 700 includes a processor 702, a non-volatile memory 704, and a network interface controller (NIC) 720. The processor 702 can execute instructions that cause the computer system 700 to implement the functionality various elements of the system 100 described above. For example, the wearable device 180 and/or the server device 110 can each take the form of the computer system 700.

Each of the components 702, 704, and 720 can be interconnected, for example, using a system bus to enable communications between the components. The processor 702 is capable of processing instructions for execution within the system 700. The processor 702 can be a single-threaded processor, a multi-threaded processor, a vector processor or parallel processor that implements a single-instruction, multiple data (SIMD) architecture, or the like. The processor 702 is capable of processing instructions stored in the volatile memory 704. In some embodiments, the volatile memory 704 is a dynamic random access memory (DRAM). The instructions can be loaded into the volatile memory 704 from a non-volatile storage, such as a Hard Disk Drive (HDD) or a solid state drive (not explicitly shown), or received via the network. In an embodiment, the volatile memory 704 can include instructions for an operating system 706 as well as one or more applications 708. It will be appreciated that the application(s) can be configured to provide the functionality of one or more components of the system 100, as described above. The NIC 720 enables the computer system 700 to communicate with other devices over a network, including a local area network (LAN) or a wide area network (WAN) such as the Internet.

It will be appreciated that the computer system 700 is merely one exemplary computer architecture and that the processing devices implemented in the system 100 can include various modifications such as additional components in lieu of or in addition to the components shown in FIG. 7. For example, in some embodiments, the computer system 700 can be implemented as a system-on-chip (SoC) that includes a primary integrated circuit die containing one or more CPU cores, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). In another embodiment, the computer system 700 can be implemented as a server device, which can, in some embodiments, execute a hypervisor and one or more virtual machines that share the hardware resources of the server device.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the embodiments as claimed.

What is claimed is:

1. A system for performing health monitoring, the system comprising:
a wearable device that includes a wireless interface; and
a server device including a memory and one or more processors configured to:
receive monitored parameter data from the wearable device via the wireless interface;
determine an artificial intelligence algorithm to use for processing the monitored parameter data;
discard one or more types of the monitored parameter data from the wearable device based on the determined artificial intelligence algorithm to generate filtered monitored parameter data;
obtain embedding data by processing health records corresponding to a user registered to the wearable device using a natural language processing algorithm, wherein the embedding data comprises an n-dimensional vector of dimensionless features obtained based on codes included in the health records corresponding to the user, and wherein the codes included in the health records comprise at least one of ICD (International Statistical Classification of Diseases) 9/10 diagnostic codes, CPT (Current Procedural Terminology) procedure codes, GPI (Generic Product Identifier) drug codes, or LOINC (Logical Observation Identifiers Names and Codes) lab codes;
process the filtered monitored parameter data and the embedding data to generate an input vector, wherein the input vector comprises a first portion corresponding to the filtered monitored parameter data and a second portion corresponding to the embedding data;
process the input vector by the artificial intelligence algorithm to generate an output vector; and
schedule an appointment with a healthcare provider based on the output vector.

2. The system of claim 1, wherein the wearable device is an activity tracker, and wherein the monitored parameter data includes data points related to one or more of:
a heart rate;
an oxygen level;
an activity level including at least one of a number of steps, a number of flights climbed, or a duration of exercise; or
a number of calories burned.

3. The system of claim 2, wherein the monitored parameter data further includes information logged by the user manually.

4. The system of claim 1, wherein the health records are stored in a database and comprise at least one of:
claims records received from a health care provider;
prescription records received from a pharmacy; or
laboratory results received from a laboratory or other health care provider.

5. The system of claim 1, wherein the input vector further includes social determinants data including one or more of:
economic information;
neighborhood information;
education information;
nutritional information; or
other environmental information.

6. The system of claim 1, wherein the input vector further includes demographic data including one or more of:
age information;
gender information;
neighborhood type information;
family size information; or
employment indicator information.

7. The system of claim 1, wherein the artificial intelligence algorithm comprises one or more of:
a multi-layer perceptron (MLP) algorithm;
a convolution neural network (CNN); or
a recurrent neural network (RNN).

8. The system of claim 1, wherein the server device is further configured to generate a notification message based on the output vector, wherein the notification message is transmitted to one of the wearable device or a mobile device associated with the wearable device to provide the user of the wearable device with a suggested action.

9. The system of claim 1, wherein the server device is further configured to generate a notification message based on the output vector, wherein the notification message is transmitted to the healthcare provider to suggest treatment options that are applicable to a patient.

10. A method for performing health monitoring, the method comprising:

receiving monitored parameter data from a wireless interface of a wearable device;

determining an artificial intelligence algorithm to use for processing the monitored parameter data;

discarding one or more types of the monitored parameter data from the wearable device based on the determined artificial intelligence algorithm to generate filtered monitored parameter data;

obtaining embedding data by processing health records corresponding to a user registered to the wearable device using a natural language processing algorithm, wherein the embedding data comprises an n-dimensional vector of dimensionless features obtained based on codes included in the health records corresponding to the user, and wherein the codes included in the health records comprise at least one of ICD (International Statistical Classification of Diseases) 9/10 diagnostic codes, CPT (Current Procedural Terminology) procedure codes, GPI (Generic Product Identifier) drug codes, or LOINC (Logical Observation Identifiers Names and Codes) lab codes;

processing the filtered monitored parameter data and the embedding data to generate an input vector, wherein the input vector includes a first portion corresponding to the filtered monitored parameter data and a second portion corresponding to the embedding data;

processing the input vector by the artificial intelligence algorithm to generate an output vector; and scheduling an appointment with a healthcare provider based on the output vector.

11. The method of claim 10, wherein the wearable device is an activity tracker, and wherein the monitored parameter data includes data points related to one or more of:

a heart rate;

an oxygen level;

an activity level including at least one of a number of steps, a number of flights climbed, or a duration of exercise; or a number of calories burned.

12. The method of claim 10, wherein the health records are stored in a database and comprise at least one of:

claims records received from the health provider;

prescription records received from a pharmacy; or laboratory results received from a laboratory or other health provider.

13. The method of claim 10, wherein the input vector further includes social determinants data including one or more of:

economic information;

neighborhood information;

education information;

nutritional information; or other environmental information.

14. The method of claim 10, wherein the input vector further includes demographic data including one or more of:

age information;

gender information;

neighborhood type information;

family size information; or employment indicator information.

15. The method of claim 10, wherein the method further comprises generating a notification message based on the output vector, wherein the notification message is transmitted to the wearable device to provide a user of the wearable device with a suggested action.

16. The method of claim 10, wherein the method further comprises generating a notification message based on the output vector, wherein the notification message is transmitted to the healthcare provider to suggest treatment options that may be applicable to a patient.

17. A non-transitory computer-readable medium having processor-executable instructions stored thereon for performing health monitoring, wherein the processor-executable instructions, when executed, facilitate:

receiving monitored parameter data from a wireless interface of a wearable device;

determining an artificial intelligence algorithm to use for processing the monitored parameter data;

discarding one or more types of the monitored parameter data from the wearable device based on the determined artificial intelligence algorithm to generate filtered monitored parameter data;

obtaining embedding data by processing health records corresponding to a user registered to the wearable device using a natural language processing algorithm, wherein the embedding data comprises an n-dimensional vector of dimensionless features obtained based on codes included in the health records corresponding to the user, and wherein the codes included in the health records comprise at least one of ICD (International Statistical Classification of Diseases) 9/10 diagnostic codes, CPT (Current Procedural Terminology) procedure codes, GPI (Generic Product Identifier) drug codes, or LOINC (Logical Observation Identifiers Names and Codes) lab codes;

processing the filtered monitored parameter data and the embedding data to generate an input vector, wherein the input vector includes a first portion corresponding to the filtered monitored parameter data and a second portion corresponding to the embedding data;

processing the input vector by the artificial intelligence algorithm to generate an output vector; and scheduling an appointment with a healthcare provider based on the output vector.

18. The non-transitory computer-readable medium of claim 17, wherein the monitored parameters include at least one of:

a heart rate;

an oxygen level;

an activity level including at least one of a number of steps, a number of flights climbed, or a duration of exercise; or a number of calories burned.

19. The non-transitory computer-readable medium of claim 17, wherein the wearable device comprises a wearable activity tracker.

20. The non-transitory computer-readable medium of claim 17, wherein the processor-executable instructions, when executed, further facilitate generating a notification message based on the output vector, wherein the notification message is transmitted to one of the wearable device or a mobile device associated with the wearable device to provide the user of the wearable device with a suggested action.

* * * * *